US007538238B2

(12) United States Patent
Akimoto et al.

(10) Patent No.: US 7,538,238 B2
(45) Date of Patent: May 26, 2009

(54) PRODUCTION METHOD OF OIL OR FAT CONTAINING POLYUNSATURATED FATTY ACID-CONTAINING TRIGLYCERIDE

(75) Inventors: Kengo Akimoto, Osaka (JP); Motoo Sumida, Uji (JP); Kenichi Higashiyama, Hyogo (JP); Shigeaki Fujikawa, Takatsuki (JP)

(73) Assignee: Suntory Limited, Osaka-shi, Osaka (JP)

( * ) Notice: Subject to any disclaimer, the term of this patent is extended or adjusted under 35 U.S.C. 154(b) by 0 days.

(21) Appl. No.: 10/482,373

(22) PCT Filed: Jul. 2, 2002

(86) PCT No.: PCT/JP02/06702

§ 371 (c)(1),
(2), (4) Date: Dec. 31, 2003

(87) PCT Pub. No.: WO03/004667

PCT Pub. Date: Jan. 16, 2003

(65) Prior Publication Data

US 2004/0171127 A1    Sep. 2, 2004

(30) Foreign Application Priority Data

Jul. 2, 2001    (JP) ............................. 2001-201357

(51) Int. Cl.
*A23D 9/00* (2006.01)
(52) U.S. Cl. ...................................... 554/224
(58) Field of Classification Search .................. 554/224
See application file for complete search history.

(56) References Cited

FOREIGN PATENT DOCUMENTS

| JP | 63-297342 | | 12/1988 |
| JP | 63/297342 | * | 12/1988 |
| JP | 06-327486 | | 11/1994 |
| JP | 8/214891 | * | 8/1996 |
| JP | 08-214891 | | 8/1996 |
| JP | 09-056379 | | 3/1997 |
| JP | 10-290699 | | 11/1998 |
| JP | 10 512444 | | 12/1998 |
| JP | 11-069974 | | 3/1999 |
| WO | 96/21037 | | 7/1996 |
| WO | WO 96/21037 | | 7/1996 |

OTHER PUBLICATIONS

Shimada, Foods & Food Ingredients Journal of Japan, No. 184, pp. 6-15, 2000.*
Shimada, JAOCS, vol. 73, No. 11, 1415-1420, 1996.*
Shimada et al., "Fatty Acid Specificity of *Rhizopus delemar* Lipase in Acidolysis," Journal of Fermentation and Bioengeneering, 1997, vol. 83, No. 4, pp. 321-327, Elsevier, New York, New York.
Yuji Shimada, "Production of Functional Lipids Containing Polyunsaturated Fatty Acids with Lipase," Foods & Food Ingredients Journal of Japan, (2000), pp. 6-15 No. 184, Japan.
Akiko Kawashima et al., "Enzymatic Synthesis of High-Purity Structured Lipids with Caprylic Acid at 1,3-Positions and Polyunsaturated Fatty Acid at 2-Position," Journal of the American Oil Chemists Society, (2001), pp. 611-616, vol. 78, No. 6, AOCS Press, Champaign, IL (USA).
Yuji Shimada et al., "Enzymatic Purification of n-6 Polyunsaturated Fatty Acids," Kagaku to Kogyo, (1999), pp. 125-130, vol. 73, No. 3, Chemical Society of Japan, Japan.
Yuji Shimada et al., "Enrichment of Arachidonic Acid: Selective Hydrolysis of a Single-Cell Oil from *Mortierella* with *Candida cylindracea* Lipase," Journal of the American Oil Chemists Society, (1995), pp. 1323-1327, vol. 72, No. 11, AOCS Press, Champaign, IL (USA).
Yuji Shimada, "Production of Functional Lipids Containing Polyunsaturated Fatty Acids with Lipase," Foods & Food Ingredients Journal of Japan, (2000), pp. 6-15, No. 184, Japan (partial translation).

* cited by examiner

*Primary Examiner*—Deborah D Carr
(74) *Attorney, Agent, or Firm*—Drinker Biddle & Reath LLP

(57) ABSTRACT

The present invention relates to a production method of an oil containing triglyceride in which medium chain fatty acids are bound to the 1- and 3-positions of the triglyceride and polyunsaturated fatty acid is bound to the 2 position by allowing lipase, which specifically acts on ester bonds at the 1- and 3-positions that has been immobilized on a porous ion exchange resin support having a pore size of about 100 Angstroms or more, to act on a mixture of medium-chain fatty acids and raw material oil containing at least one polyunsaturated fatty acid selected from the group consisting of ω6 series polyunsaturated fatty acid having 18 or more carbon atoms and 3 or more double bonds and ω9 series polyunsaturated fatty acid having 18 or more carbon atoms and 2 or more double bonds, but not containing ω3 series polyunsaturated fatty acid, oils and fats or triglycerides obtained by that method, and the use of the oils and fats or triglycerides in a food, beverage or pharmaceutical composition.

8 Claims, No Drawings

PRODUCTION METHOD OF OIL OR FAT CONTAINING POLYUNSATURATED FATTY ACID-CONTAINING TRIGLYCERIDE

BACKGROUND OF THE INVENTION

1. Technical Field

The present invention relates to an oil or fat containing a triglyceride in which medium-chain fatty acids are bound to positions 1 and 3 of the triglyceride and at least one type of polyunsaturated fatty acid, selected from the group consisting of ω6 series polyunsaturated fatty acids having 18 or more carbon atoms and 3 or more double bonds and ω9 series polyunsaturated fatty acids having 18 or more carbon atoms and 2 or more double bonds, is bound to the 2 position, a production method thereof, and a composition containing these oils or fats.

2. Background Art

Eicosapentaenoic acid (to be referred to as "EPA") and docosahexaenoic acid (to be referred to as "DHA") are known to be ω3 series polyunsaturated fatty acids that have numerous physiological functions such as preventive effects on adult diseases such as arteriosclerosis and thrombosis, an anticancer action and an action that enhances learning acquisition, and they have been used in pharmaceuticals and foods for specified health uses. However, there has recently been a growing interest in the physiological functions of polyunsaturated fatty acids other than ω3 series polyunsaturated fatty acids (such as ω6 series and ω9 series polyunsaturated fatty acids).

The pathway by which polyunsaturated fatty acids are biosynthesized in humans consists of two representative series, namely the ω3 series and ω6 series (ω refers the number of the carbon atom where the first double bond is located counting from the methyl terminal end of the fatty acid). Known examples of ω6 series polyunsaturated fatty acids include linoleic acid, γ-linolenic acid, dihomo-γ-linolenic acid and arachidonic acid.

Arachidonic acid accounts for about 10% of the fatty acids that compose important organs such as the blood and liver (for example, arachidonic acid accounts for 11%, eicosapentaenoic acid 1% and docosahexaenoic acid 3% of the fatty acid composition in the phospholipids of human blood), is involved in regulation of membrane fluidity as a major constituent of the cell membrane, and demonstrates various functions involved in the body's metabolism. On the other hand, it also plays an important role as a direct precursor of prostaglandins. Recently, attention has been focused in particular on the role of arachidonic acid as an infant nutrient by serving as a constituent fatty acid of endogenous cannabinoids that exhibit neurergic action (such as 2-arachidonoyl monoglycerol and anandamide). Although humans are unable to synthesize linoleic acid, following ingestion of vegetable oils, unsaturation and lengthening of the carbon chain are repeated resulting in conversion to γ-linolenic acid, dihomo-γ-linolenic acid and arachidonic acid. Thus, an adequate amount of arachidonic acid is normally synthesized if a diet rich in linoleic acid is consumed. However, in patients with adult diseases, persons susceptible to adult diseases, infants and the elderly, as the activity of enzymes involved in biosynthesis decreases, thus causing a shortage of arachidonic acid, it is preferable to ingest arachidonic acid directly in the form of a composite fatty acid of oils and fats (triglycerides).

Although ingested oils and fats (triglycerides) are typically hydrolyzed by pancreatic lipase when they enter the small intestine, this pancreatic lipase is specific for the 1,3 positions, enabling the 1,3-positions of the triglycerides to be severed resulting in the formation of two molecules of free fatty acid, while at the same time forming one molecule of 2-monoacylglycerol (to be referred to as "2-MG"). Since this 2-MG is extremely soluble in bile acids and has a high degree of absorption, 2-position fatty acids are typically considered to be easily absorbed. In addition, when 2-MG dissolves in bile acids, it plays the role of a surfactant by acting to increase the absorption of free fatty acids. Next, the free fatty acids and 2-MG biosynthesize bile acid compound micelles together with cholesterol and phospholipids, which are then incorporated into small intestine epithelial cells where the resynthesis of triacylglycerol takes place, after which this is ultimately released into the lymph in the form of chylomicrons.

However, persons that require arachidonic acid at the same time also have weak activity of pancreatic lipase (for example, pancreatic lipase activity is also known to decrease with aging), which is responsible for the first stage of oil/fat (triglyceride) absorption, and are unable absorb adequate amounts of arachidonic acid from foods and oils and fats containing arachidonic acid (including arachidonic-acid containing oils and fats in the form of microbial fermented oils and fats).

Therefore, triglycerides in which medium-chain fatty acids, which are easily hydrolyzed by pancreatic lipase, are bound to the 1,3-positions of triglycerides and arachidonic acid is bound to the 2-position are the optimum oils and fats (triglycerides) for persons requiring arachidonic acid. Although Japanese Unexamined Patent Publication No. 8-214891 discloses a production method of an oil or fat containing triglyceride that contains polyunsaturated fatty acid wherein medium-chain fatty acids are bound to the 1,3-positions and a polyunsaturated fatty acid is bound to the 2-position, the only concrete description is that of a production method of triglyceride in which EPA or DHA is bound to the 2 position, while there is no specific disclosure whatsoever of a production method of triglyceride in which arachidonic acid is bound to the 2-position.

Japanese Unexamined Patent Publication No. 2000-270885 discloses a method for producing a structural lipid in which the number of carbon atoms of the fatty acids bound to the 1- and 3-positions of the target triglyceride is 12 or less, and 90% or more of the fatty acids bound to the 2-position are polyunsaturated fatty acids by allowing lipase to specifically act on the 1,3-positions of the triglyceride. Here, the oil or fat that allows the lipase to act is, for example, triglycerides in which 98% or more is EPA triglyceride, and this is synthesized by allowing non-position-specific lipase to act on glycerin and a polyunsaturated fatty acid or lower alcohol ester thereof while dehydrating. However, in the above method, although a highly pure polyunsaturated fatty acid or lower alcohol ester thereof is required instead of a mixture, as it is still difficult to obtain these inexpensively, it is not realistic to produce a target product by the aforementioned method.

On the other hand, a method is known for inexpensively producing an oil or fat (triglyceride) containing polyunsaturated fatty acid by fermentation. A production method of triglyceride in which caprylic acid is bound to the 1- and 3-positions, utilizing this microbial oil, was disclosed by Yuji Shimada (Journal of Fermentation and Bioengineering, 83, 321-327 (1997) "Fatty Acid Specificity of *Rhizopus delemar* Lipase in Acidolysis") wherein a microbial oil containing 25% by weight of arachidonic acid that was available at the time as substrate was fermented by 1,3-position specific type lipase. However, as the position where the arachidonic acid binds to the triglyceride of this microbial oil is random, even if fatty acid at the 1- and 3-positions is nearly completely substituted by caprylic acid by the enzyme, the proportion of 1,3-capryolyl-2-arachidonoyl-glycerol (to be referred to as "8A8") in the resulting oil does not exceed the proportion of arachidonic acid bound to the 2-position of the raw material oil even at the maximum level. In this case, the proportion of the arachidonic acid bound to the 2-position is at most 25% by weight and, in actuality, as there are also triglycerides present in which arachidonic acid is bound at multiple locations, the proportion of arachidonic acid bound to the 2-position is 25% by weight or less. According to the report by Shimada, et al. (Journal of Fermentation and Bioengineering, 83, 321-327 (1997)), although the resulting triglyceride was analyzed by high-performance liquid chromatography, as the retention times of 8A8, 1,3-capryloyl-γ-linolenoyl-glycerol (to be referred to as "8G8") and 1,3-capryloyl-2-dihomo-γ-linolenoyl-glycerol (to be referred to as "8D8") are the same, the proportion of 8A8 in the triglyceride was not accurately determined. However, as the total of 8A8, 8G8 and 8D8 was about 20 mol %, the resulting triglyceride was not satisfactory with respect to containing 25 mol % or more of 8A8.

In the case of using a microbial oil as a raw material oil in this manner, as the position where arachidonic acid binds to triglyceride is random, it is necessary to use, for the raw material, a triglyceride having a higher content of arachidonic acid in order to enhance the proportion of the target 8A8.

However, the reactivity of 1,3-position specific type lipase to fatty acid decreases the longer the length of the carbon chain and the greater the number of double bonds. In addition, the location of the double bonds, in terms of the carbon atoms at which double bonds are inserted when counting from the carboxyl group, is also an important element when discussing the reactivity of lipase. For example, although lipase exhibits a high level of reactivity with α-linolenic acid 9,12,15-octadecatrienoic acid), it exhibits extremely low reactivity with γ-linolenic acid (6,9,12-octadecadienoic acid), and although it exhibits high reactivity with DPA ω3 series (7,10,13,16,19-docosapentaenoic acid), it exhibits extremely low reactivity with DPA ω6 series (4,7,10,13,16-docosapentaenoic acid). Namely, lipase has the problem of exhibiting low reactivity with unsaturated fatty acids having 3 or more double bonds in the case of ω6 series polyunsaturated fatty acids having 18 or more carbon atoms, and unsaturated fatty acids having 2 or more double bonds in the case of ω9 series unsaturated fatty acids. Thus, in order to obtain an oil or fat containing a higher concentration of a target triglyceride in which medium-chain fatty acids are bound to the 1,3-positions and at least one polyunsaturated fatty acid, selected from the group consisting of ω6 series polyunsaturated fatty acid having 18 or more carbon atoms and 3 or more double bonds, and ω9 series polyunsaturated fatty acid having 18 or more carbon atoms and 2 or more double bonds, is bound to the 2-position, it is necessary to use an oil or fat containing a higher concentration of at least one type of polyunsaturated fatty acid, selected from the group consisting of ω6 series polyunsaturated fatty acid having 18 or more carbon atoms and 3 or more double bonds and ω9 series polyunsaturated fatty acid having 18 or more carbon atoms and 2 or more double bonds, for the raw material oil or fat. However, the higher the content of this oil or fat, the lower the reactivity and the poorer the reaction yield. This decrease in the reaction yield results in the formation of a large amount of unreacted triglyceride (raw material triglyceride and triglyceride in which only one of the fatty acids at the 1,3-positions have become a medium-chain fatty acid), and as a result, the proportion of the target triglyceride cannot be increased. Thus, there is a strong need for the development of a practical method for increasing the proportion of target triglyceride.

The ω6 series polyunsaturated fatty acid, dihomo-γ-linolenic acid, is expected to demonstrate precursor effects on type I prostaglandins, antithrombotic action, blood pressure lowering action, antidyskinetic action, anti-inflammatory action, delayed allergy inhibitory effects, skin protective action and anticancer action as its independent physiological actions. Thus, although there has similarly been a need for the development of triglyceride in which medium-chain fatty acids are bound to the 1,3-positions and dihomo-γ-linolenic acid is bound to the 2-position, the existence of oils and fats (triglycerides) having a high content of dihomo-γ-linolenic acid is not known, and there are no known findings whatsoever regarding the production of triglyceride for that purpose.

Fatty acids of ω9 series polyunsaturated fatty acids such as 5,8,11-eicosatrienoic acid (20:3 ω9 series, to be referred to as Mead acid) and 8,11-eicosadienoic acid (20:2 ω9 series) are known to be present as one of the constituent fatty acids in animal tissue deficient in essential fatty acids. However, since they are only present in minute amounts, their isolation and purification has been extremely difficult. These polyunsaturated fatty acids are able to become precursors of the leucotriene 3 group in the body, and their physiological activity is the target of considerable expectation and reported examples of which include anti-inflammatory, antiallergic and antirheumatic action (Japanese Unexamined Patent Publication No. 7-41421). Thus, although there is similarly a need for the development of triglycerides in which medium-chain fatty acids are bound to the 1,3-positions and ω9 series polyunsaturated fatty acid is bound to the 2-position, the existence of oils and fats (triglycerides) having a high content of 09 series polyunsaturated fatty acid is unknown, and there are no known findings whatsoever relating to the production of a triglyceride for that purpose.

DISCLOSURE OF THE INVENTION

The object of the present invention is to provide an oil or fats containing triglyceride in which medium-chain fatty acids are bound to the 1,3-positions, and at least one type of polyunsaturated fatty acid, selected from the group consisting of ω6 series polyunsaturated fatty acid having 18 or more carbon atoms and 3 or more double bonds and ω9 series polyunsaturated fatty acid having 18 or more carbon atoms and 2 or more double bonds, is bound to the 2 position, a production method thereof and a composition containing these oils or fats.

As a result of first conducting extensive research on an industrial production method of an oil or fat (triglyceride) containing 40% by weight or more of arachidonic acid in order to achieve the objective of producing an oil or fat containing 25 molt or more of triglyceride in which medium-chain fatty acids are bound to the 3-position and arachidonic acid is bound to the 2-position, the inventors of the present invention surprisingly obtained an oil or fat (triglyceride) containing 45% by weight or more of arachidonic acid by controlling the concentration of the carbon source in the medium.

Moreover, as a result of conducting extensive research in order to achieve the objective of producing an oil of fat containing a high content of triglyceride in which medium-chain fatty acids are bound to the 1,3-positions and dihomo-γ-linolenic acid or ω9 series polyunsaturated fatty acid is bound to the 2-position, an oil or fat (triglyceride) was obtained that contained a high content of dihomo-γ-linolenic acid or ω9 series polyunsaturated fatty acid by using a mutant strain of an arachidonic acid-producing microorganism.

Moreover, as a result of conducting extensive research with the aim of improving enzyme reaction efficiency, the inventors of the present invention surprisingly succeeded in improving a reaction efficiency by raising the reaction temperature.

Moreover, the inventors of the present invention succeeded in acquiring an immobilized enzyme having high thermal stability by selecting an immobilizing support, which made it possible to use the enzyme at a high reaction temperature, thereby leading to completion of the present invention. In addition, the laboratory results obtained for these methods can easily be scaled up to provide a method suitable for industrial production of the aforementioned oil or fat.

Thus, the present invention provides oils and fats containing triglyceride in which medium-chain fatty acids are bound to the 1- and 3-positions of the triglyceride, and at least one polyunsaturated fatty acids, selected from the group consisting of ω6 series polyunsaturated fatty acid having 18 or more carbon atoms and 3 or more double bonds and ω9 series polyunsaturated fatty acid having 18 or more carbon atoms and 2 or more double bonds, is bound to the 2-position, a production method thereof and a composition containing these oils or fats.

According to the present invention, for example, an oil or fat containing 25 mol % or more of triglyceride in which medium-chain fatty acids are bound to the 1,3-positions and arachidonic acid is bound to the 2-position, an oil or fat containing triglyceride in which medium-chain fatty acids are bound to the 1,3-positions and dihomo-γ-linolenic acid is bound to the 2-position, or an oil or fat containing triglyceride in which medium-chain fatty acids are bound to the 1,3-positions and ω9 series polyunsaturated fatty acid is bound to the 2-position, can be produced, they can be widely used in pharmaceuticals, foods for specified health uses and so forth due to the numerous physiological functions of these oils and fats, and are industrially extremely useful.

BEST MODE FOR CARRYING OUT THE INVENTION

The present invention relates to a method for producing an oil or fat containing triglyceride in which medium-chain fatty acids are bound to the 1,3-positions and a polyunsaturated fatty acid is bound to the 2-position by transesterification of long-chain fatty acids that constitute the 1,3-positions of oil or fat (triglyceride) containing polyunsaturated fatty acid to medium-chain fatty acids, and to an oil or fat containing triglycerides in which medium-chain fatty acids are bound to the 1,3-positions and polyunsaturated fatty acid is bound to the 2-position.

In the present invention, in order to prevent a decrease in the reaction yield caused by an increase in unreacted oil or fat (raw material triglyceride and triglyceride in which only one of the fatty acids of the 1,3-positions has become a medium-chain fatty acid) accompanying an increase in the proportion of polyunsaturated fatty acid in the oil or fat (triglycerides) serving as the raw material, the enzyme reaction temperature should be 30-50° C., and preferably 40-50° C.

Examples of lipases that can be used in the present invention which specifically act on the ester bonds of the 1,3-positions of the triglycerides include those produced by microorganisms belonging to the genii Rhizopus, Rhizomucor and Aspergillus, as well as porcine pancreatic lipase. Commercially available products can be used for these lipases. Examples of commercially available products include, but are not limited to, the lipase of *Rhizopus delemar* (Tanabe Seiyaku), and the lipases of *Rhizomucor miehei* (Novo Nordisk, Lipozyme IM) and *Aspergillus niger* (Amano Pharmaceutical, Lipase A), and any lipase can be used provided it is specific for the 1,3-positions.

The aforementioned lipase is used in the form of lipase immobilized on a immobilizing support for the purpose of imparting heat resistance to the enzyme in order to allow the reaction temperature to be 30° C. or higher, and preferably 40° C. or higher, for the purpose of enhancing reaction efficiency. Although celite or ceramics have been used as immobilizing supports, in the present invention, as a result of studying immobilizing supports suitable for imparting heat resistance, a porous ion exchange resin having a pore size of about 100 Angstroms or more was confirmed to be effective.

The inventors of the present invention selected the aforementioned immobilizing support by the process described below. Namely, an ion exchange resin is used to purify the protein, and the protein is fractioned based on the principle of adsorbing and desorbing protein based on ionic bonding. By using this principle, the inventors of the present invention reasoned that it would be possible to immobilize enzyme in the form of protein by adsorbing it to an ion exchange resin. Hydrophilic resin supports, namely polysaccharide supports such as cellulose or Sepharose®, are commonly used for protein purification. However, the hydrophilic property becomes a hindrance to transesterification of oils or fats. Therefore, as a result of conducting extensive studies, a polymer-type or ceramic-type resin thought to have superior lyophilicity was considered to be suitable for this selection. These ion exchange resins are primarily used for aqueous treatment, and have not been used for adsorptive purification of enzymes. Next, the ion exchange resins are divided into anionic exchange resins and cationic exchange resins. When the group of target lipases were adsorbed to both ion exchange resins, they were found to be reliably adsorbed onto the anionic exchange resin. Moreover, when enzyme was adsorbed onto an anionic exchange type of polymer resin, polymer types of ion exchange resins rather than gel types resulted in adsorption of more enzyme, thereby making it possible to immobilize enzyme with high activity. The pore size of these polymer type resins can be changed depending on the combination of the raw materials consisting of styrene, vinylbenzene, phenols, acrylics, plasticizer and so forth. Since these anionic exchange resins consist of weakly basic and strongly basic types, results are shown for studies conducted using representative anionic exchange resins.

The microbial oil (having a triglyceride content of 95% or more) containing 40% by weight of arachidonic acid shown below was allowed to enzymatically react with caprylic acid, and after reacting for 2 days at 40° C., the degrees of enzyme activity were compared based on the amount of caprylic acid (mol %) incorporated in the triglycerides. The reaction conditions were as shown below.

| | |
|---|---|
| Arachidonic acid-containing oil (SUNTGA40S) | 1.33 g |
| Caprylic acid | 2.66 g |
| Immobilized enzyme | 0.2 g |

Reacted for 48 hours at 40° C. while shaking (Analysis)

Following completion of the reaction, the reaction liquid and immobilized enzyme were separated and the reaction liquid was extracted to alkalinity with hexane. A portion of the extracted triglyceride fraction was methylated with sodium methylate to obtain fatty acid methyl ester. The resulting fatty acid methyl ester was analyzed by gas chromatography (GC) to assay the amount of methyl caprylate. As the raw material arachidonic acid-containing oil did not contain caprylic acid, the caprylic acid incorporated by enzyme activity can be measured by GC. In this manner, enzyme activity was indicated as the proportion of caprylic acid (mol %) of the value determined by GC analysis following completion of the reaction.

| Immobilized enzyme support | Type | 8:0 (Caprylic acid) |
|---|---|---|
| Dowex Marathon WBA | Weakly anionic, porous | 50.9 |
| Dowex Marathon A | Strongly anionic, gel | 42.1 |
| SM-10 | Ceramic | 48.7 |
| Amberlite IRA904 | Strongly anionic, porous | 33.5 |
| Diaion WA 10 | Weakly anionic, gel | 40.1 |
| Diaion WA 30 | Weakly anionic, porous | 49.8 |

In the above table, the ion exchange resins of Dow Chemical are defined as macroporous in the case of having a pore size of 100 to 1000 Angstroms, and as a gel in the case of having a pore size of 100 Angstroms or less. Mitsubishi Chemical defines those having a pore size of 300 Angstroms or more as being macroporous. Thus, Dowex Marathon WBA (trade name, Dow Chemical) is an ion exchange resin having a pore size of 100 Angstroms or more.

When the properties of Dowex Marathon WBA (trade name, Dow Chemical) were confirmed, because this resin demonstrated satisfactory results, it was determined to be effective with respect to the following factors.

1. It is a porous resin having a pore size of 100 Angstroms or more.
2. The advantages of porous types exceeded those of gel types based on comparisons between Dowex Marathon WBA (trade name, Dow Chemical) and Dowex Marathon A (trade name, Dow Chemical), and between Diaion WA 10 (trade name, Mitsubishi Chemical) and Diaion WA 30 (trade name, Mitsubishi Chemical).
3. Although immobilized enzyme can be prepared by having anionic exchange groups based on a comparison between Dowex Marathon WBA (trade name, Dow Chemical) and Dowex Marathon A, (trade name, Dow Chemical), it is more advantageous to have weakly basic anionic exchange groups rather than strongly basic groups when producing more preferable highly active forms.
4. As the ion exchange capacity of Amberlite IRA904 (trade name, Rohm and Haas) is less than that of Dowex Marathon WBA (trade name, Dow Chemical), the resulting activity was even lower.

On the basis of these factors, the preferable form of an immobilizing support is not a gel, but rather a porous (highly porous) resin having numerous pores of 100 Angstroms or more, and preferably a support having weakly basic cationic exchange groups rather than strongly basis groups while also having a high ion exchange capacity.

Moreover, this support preferably has lyophilic properties in consideration of it being used for enzymatic conversion of lipids. As the enzyme reaction takes place within an oil or fat, enzyme immobilized in the pores is also able to participate in the reaction as a result of the raw material oils or fats entering the lyophilic resin, thereby increasing the reaction rate and improving reaction efficiency. In turn, as the time during which an enzyme susceptible to heat is exposed to heat during the course of the reaction is shortened, together with this leading to extension of enzyme life, this can also be said to be a suitable method for improving productivity.

The aforementioned ion exchange resins are only meant to serve as examples, and resins are continuously evolving and even better resins are appearing on the market. In the case such an improved type becomes available, it is clear that it would have activity equal to or greater than that of Dowex Marathon WBA (trade name, Dow Chemical).

In the present specification, although Dowex Marathon WBA (trade name, Dow Chemical) is used for the ion exchange resin, the resin is not limited to this immobilizing support, but rather all such resins may be used provided they are ion exchange resins capable of imparting heat resistance equal to or greater than that of the aforementioned resin.

In addition, an object of the present invention is to efficiently produce triglycerides in which medium-chain fatty acids are ester bound to the target 1,3-positions and polyunsaturated fatty acid is ester bound to the 2-position without causing a decrease in reaction efficiency and while maintaining position specificity even in the case of oils or fats containing polyunsaturated fatty acid for which 1,3-position specific type lipase exhibits low reactivity by using an immobilized enzyme having heat resistance. Thus, a method for imparting heat resistance other than selection of the immobilizing support can also be used, an example of which is the imparting of a high level of heat resistance by treating the immobilized enzyme with a crosslinking agent such as genipin crosslinking agent.

For one part of immobilizing support, an immobilizing support is suspended in 0.5-20 parts by weight of an aqueous solution of 1,3-position specific type lipase followed by the gradual addition of 2-5 parts of cold acetone (e.g., −80° C.) to the suspension while stirring to form a precipitate. An immobilized enzyme can then be prepared by drying this precipitate under reduced pressure. As an even simpler method, 0.05-0.4 parts of 1,3-position specific type lipase are dissolved in a minimum of water and mixed with 1 part of immobilizing support while stirring followed by drying under reduced pressure to prepare an immobilized enzyme. Although about 90% of the lipase is immobilized on the support by this procedure, since it does not exhibit any transesterification activity in this state, the immobilized enzyme can be activated most efficiently by pre-treating in a substrate (raw material oil or fat and medium-chain fatty acids) to which 1-10% water has been added, and preferably in a substrate to which 1-3% water has been added, followed by use in production.

Depending on the type of enzyme, the amount of water added to the reaction system is extremely important. The transesterification proceeds with difficulty if water is not contained in the reaction system, while hydrolysis occurs if a large amount of water is present, thereby decreasing the triglyceride recovery rate (due to the formation of diglycerides and monoglycerides by hydrolysis). In this case, however, by using an immobilized enzyme that has been activated by the aforementioned pre-treatment, the amount of water added to the reaction system is no longer important, and the transesterification reaction occurs efficiently even in the complete absence of water. Moreover, activation treatment of the immobilized enzyme by water can also be omitted by selecting the type of enzyme agent.

A raw material oil or fat serving as a substrate for the lipase in the present invention refers to an oil or fat that contains at least one polyunsaturated fatty acid selected from the group consisting of ω6 series polyunsaturated fatty acid having 18 or more carbon atoms and 3 or more double bonds and ω9 series polyunsaturated fatty acid having 18 or more carbon atoms and 2 or more double bonds, but does not contain ω3 series polyunsaturated fatty acid, and an oil or fat containing 80% by weight or more, preferably 90% by weight or more, and more preferably 95% by weight or more, of triglycerides can be used for said oil.

As a result of the present invention raising the enzyme reaction temperature by using an immobilized enzyme having heat resistance, the target triglycerides can be produced efficiently without causing a decrease in reaction efficiency even in the case of an oil or fat of the present invention that contains polyunsaturated fatty acid having a low level of reactivity. Thus, in the present invention, even an oil or fat can be used in which the total amount of at least one polyunsaturated fatty acid selected from the group consisting of ω6 series polyunsaturated fatty acid having 18 or more carbon atoms and 3 or more double bonds and ω9 series polyunsaturated fatty acid having 18 or more carbon atoms and 2 or more double bonds 30% by weight or more, 42% by weight or more, or 50% by weight or more, relative to the total amount of fatty acid in said oil or fat. Furthermore, examples of ω6 series polyunsaturated fatty acid having 18 or more carbon atoms and 3 or more double bonds include arachidonic acid and dihomo-γ-linolenic acid, while examples of ω9 series polyunsaturated fatty acid having 18 or more carbon atoms and 2 or more double bonds include 6,9-octadecaenoic acid, 8,11-eicosadienoic acid and 5,8,11-eicosatrienoic acid.

In addition, an oil or fat can be obtained that contains triglycerides in which medium-chain fatty acids are bound to the 1,3-positions and polyunsaturated fatty acid is bound to the 2-position at a higher concentration the higher the content of the same polyunsaturated fatty acid in the raw material oil or fat. More specifically, an oil or fat can be used that contains the same polyunsaturated fatty acid at 15% by weight or more, preferably 25% by weight or more and more preferably 30% by weight or more, relative to the total amount of fatty acid in the oil or fat. More specifically, an oil or fat can be used that contains arachidonic acid at 25% by weight or more, preferably 30% by weight or more, more preferably 40% by weight or more, even more preferably 45% by weight or more and the most preferably 50% by weight or more, relative to the total amount of fatty acid in the oil or fat.

In addition, oil produced by microorganisms can be used for the raw material oil or fat of the present invention. Microorganisms that produce at least one polyunsaturated fatty acid from among ω6 series polyunsaturated fatty acid having 18 or more carbons and 3 or more double bonds and ω9 series polyunsaturated fatty acid having 18 or more carbon atoms and 2 or more double bonds primarily as constituent fatty acid of triglycerides are preferably used as microorganisms.

Examples of microorganisms having the ability to produce arachidonic acid include microorganisms belonging to the genii *Mortierella, Conidiobolus, Pythium, Phytophthora, Penicillium, Cladosporium, Mucor, Fusarium, Aspergillus, Rhodotorula, Entomophthora, Echinosporangium* and *Saprolegnia*. Examples of microorganisms belonging to the genus *Mortierella* subgenus *Mortierella* include *Mortierella elongata, Mortierella exigua, Mortierella hygrophila* and *Mortierella alpina*. Specific examples of these strains include *Mortierella elongata* IF08570, *Mortierella exigua* IF08571, *Mortierella hygrophila* IF05941 and *Mortierella alpina* IF08568, ATCC16255, ATCC32221, ATCC42430, CBS219.35, CBS224.37, CBS250.53, CBS343.66, CBS527.72, CBS529.72, CBS608.70 and CBS754.68.

All of the these strains can be acquired without restriction from the Institute for Fermentation (IFO), Osaka, Japan, the American Type Culture Collection (ATCC), USA and the Centrralbureau voor schimmelcultures (CBS). In addition, the strain *Mortierella elongata* SAM0219 (NIBH Deposit No. FERM P-8703) (NIBH Deposit No. FERM BP-1239), which was isolated from the soil by the same research group that made the present invention, can also be used.

In order to culture the microbial strains used in the present invention, spores or mycelia of that microbial strain or a pre-culture liquid obtained by culturing the microbial strain in advance are inoculated into liquid or solid media. In the case of liquid media, although glucose, fructose, xylose, saccharose, maltose, soluble starch, molasses, glycerol, mannitol or the like are typically used as a carbon source, any of these may be used and there are no restrictions on them. Examples of nitrogen sources that can be used include natural nitrogen sources such as peptones, yeast extract, wheat germ extract, beef extract, casamino acids, cornstarch stiplica, soybean protein, defatted soybean and cottonseed residue, as well as organic nitrogen sources such as urea, and inorganic nitrogen sources such as sodium nitrate, ammonium nitrate and ammonium sulfate. In addition, inorganic salts such as phosphates, magnesium sulfate, iron sulfate and copper sulfate as well as vitamins and so forth can be used as necessary as trace nutrient sources. There are no particular restrictions on these media ingredients provided they are at a concentration that does not impair microorganism growth. In practical terms, the nitrogen source should typically have a concentration of 0.1-40% by weight, and preferably 1-25% by weight. The initial amount of nitrogen source added is typically 0.1-10% by weight, and preferably 0.1-6% by weight, and the nitrogen source may be added during the course of culturing.

A method for industrial production of oils and fats containing arachidonic acid using a strain of microorganisms belonging to the genus *Mortierella* subgenus *Mortierella* has already been established ("Enhancement of Arachidonic Acid Production by *Mortierella alpina* 1S-4", J. Am. Oil Chem. Soc., 75, pp. 1501-1505 (1998), "Effects of Mineral Addition on the Growth Morphology of and Arachidonic Acid Production by *Mortierella alpina* 1S-4", J. Am. Oil Chem. Soc., 75, pp. 1815-1819 (1998)). However, as the proportion of arachidonic acid relative to the total amount of fatty acid is a maximum of 45% by weight, it is preferable that the arachidonic acid of the raw material oils and fats be present at 45% by weight or more in order to produce an oil or fat (triglycerides) that contains 25 mol % or more, or 30 mol % or more, of the 8A8 of the present invention by an enzymatic method. An effective means of increasing the proportion of arachidonic acid is to deplete the carbon source in the medium. When the carbon source in the medium is depleted, the microorganisms assimilate the accumulated oils and fats and, as assimilation begins with saturated fatty acids, the proportion of arachidonic acid in the triglyceride ultimately increases. Although this type of approach is possible in theory, in actuality, the amount of oils and fats (triglycerides) produced that contains a high content of arachidonic acid is extremely low due to assimilation of triglyceride, making this method completely impractical as a production method for supplying reaction substrate. Therefore, the inventor of the present invention succeeded in industrially producing oils and fats (triglycerides) that contains 45% by weight or more of arachidonic acid by controlling the concentration of carbon source in the medium. Culturing consists of an organism growth phase extending from days 2 to 4 of culturing, and an oils and fats accumulation phase extending beyond days 2 to 4 of culturing. The initial concentration of the carbon source should be 1-8% by weight, and preferably 2-4% by weight, the carbon source should be gradually increased only during the organism growth phase and early oils and fats accumulation stage, and total amount of the sequentially added carbon source should be 2-20% by weight, and preferably 5-15% by weight. Furthermore, a method for industrial production of an oil or fat (triglycerides) having a target arachidonic acid content of 45% by weight or more has been established by making the gradually added amount of carbon source added during the organism growth phase such that the concentration of carbon source in the medium becomes 0 on day 7 of culturing and beyond, preferably on day 6 of culturing and beyond, and more preferably on day 4 of culturing and beyond, by adding the amount of the carbon source depending on the initial concentration of the nitrogen source.

Although the culturing temperature of arachidonic acid-producing microorganisms varies according to the microorganism used, it should be 5-40° C. and preferably 20-30° C., and after growing the microorganisms by culturing at 20-30° C., culturing is continued at 5-20° C. to produce unsaturated fatty acid. The proportion of polyunsaturated fatty acids among the fatty acids formed can be increased by controlling the temperature in this manner. The pH of the medium is 4-10, and preferably 5-9, and culturing is carried out by aerated stir culturing, shake culturing or stationary culturing. Culturing is normally carried out for 2-30 days, preferably 5-20 days, and more preferably 5-15 days.

As another means of increasing the proportion of arachidonic acid in oils and fats containing arachidonic acid besides controlling the concentration of the carbon source in the medium, oils and fats having a high content of arachidonic acid can also be obtained by selectively hydrolyzing oils and fats containing arachidonic acid. Since the lipase used for this selective hydrolysis does not have position specificity for triglycerides, and the hydrolysis activity decreases in proportion to the number of double bonds, ester bonds of fatty acids other than polyunsaturated fatty acids are hydrolyzed. The resulting triglyceride has an increased polyunsaturated fatty acid content due to the occurrence of a transesterification reaction between the resulting polyunsaturated fatty acid partial glycerides ("Enhancement of Arachidonic Acid: Selective Hydrolysis of a Single-Cell Oil from *Mortierella* with *Candida cylindracea* Lipase", J. Am. Oil Chem. Soc., 72, 1323-1327 (1998)). In this manner, an oil or fat having a high content of arachidonic acid obtained by carrying out selective hydrolysis on an oil or fat containing arachidonic acid can be used as the raw material oil or fat of the present invention. A raw material oil or fat can be used as a raw material oil or fat of the present invention provided it has an arachidonic acid content of 25% by weight or more, preferably 30% by weight or more, more preferably 40% by weight or more, even more preferably 45% by weight or more, and most preferably 50% by weight or more, and is not limited to that obtained by methods described in the specification.

Moreover, the present invention is also able to use an oil or fat (triglycerides) containing dihomo-γ-linolenic acid or ω9 series polyunsaturated fatty acid as a raw material oil or fat.

A method for efficiently producing oil or fat (triglycerides) containing dihomo-γ-linolenic acid has already been developed by the inventors of the present invention (Japanese Unexamined Patent Publication No. 5-91887). Moreover, with respect to a method for efficiently producing an oil or fat (triglycerides) containing ω9 series polyunsaturated fatty acid (such as 6,9-octadecaenoic acid (18:2 ω9), 8,11-eicosaenoic acid (20:2 ω9) or 5,8,11-eicosatrienoic acid (20:3 ω9)), methods for producing an oil or fat containing ω9 series polyunsaturated fatty acid by using a mutant strain in which Δ12 unsaturation enzyme is depressed or missing, which is obtained by performing mutation treatment on microorganisms belonging to the genus *Mortierella* subgenus *Mortierella*, have been developed by the inventors of the present invention (Japanese Unexamined Patent Publication No. 5-91888, Japanese unexamined Patent Publication No. 10-57085, and Japanese Unexamined Patent Publication No. 5-91886). However, there is nothing whatsoever described regarding the production of an oil or fat (triglycerides), in which medium-chain fatty acids are bound to the 1,3-positions and polyunsaturated fatty acid is bound to the 2-position, by using, for the raw material, an oil or fat containing polyunsaturated fatty acid, and it was produced for the first time in the present invention. Furthermore, an oil or fat in which the proportion of dihomo-γ-linolenic acid or ω9 series polyunsaturated fatty acid has been increased by the method involving control of the concentration of the carbon source in the medium or the method involving the obtaining of an oil or fat having a high arachidonic acid content by selectively hydrolyzing an oil or fat containing arachidonic acid, which were used as means of increasing the proportion of arachidonic acid in an oil or fat containing arachidonic acid, can also be used as raw material oil or fat.

Medium chain fatty acids selected from fatty acids having 6 to 12 carbon atoms can be used for the medium-chain fatty acids used in the present invention. Examples of medium-chain fatty acids having 6 to 12 carbon atoms include caprylic acid and capric acid, as well as their lower alcohol esters and oils and fats having fatty acids of 6 to 12 carbon atoms as composite fatty acids, and they can be used in any form.

Although the reaction yield in the present invention has been increased as much as possible by raising the reaction temperature as a result of using an immobilized enzyme having heat resistance in which deterioration of activity does not occur, the reaction yield can be further increased by repeatedly carrying out the aforementioned transesterification reaction. More specifically, after allowing immobilized enzyme to act on a mixture of raw material oil or fat and medium-chain fatty acids, the immobilized enzyme (lipase imparted with heat resistance) is recovered from the reaction product followed by removal of free fatty acids by superfractionation or extraction with alkaline hexane and then adding medium-chain fatty acids to the resulting oil or fat to obtain a reaction product by allowing the previously recovered immobilized enzyme to act on the medium-chain fatty acids. As a result of using this method, the reaction efficiency increases and an oil or fat can be obtained that contains 80% or more of triglyceride in which medium-chain fatty acids are bound to the 1,3-positions. There are no restrictions on the number of reactions of the aforementioned steps, and the reaction can be carried out many times provided the enzyme does not lose activity.

The enzyme reaction of the present invention may be carried out in batches or continuously provided a triglyceride is obtained in which medium-chain fatty acids are bound to the 1,3-positions and a polyunsaturated fatty acid is bound to the 2-position. Moreover, in the case of a batch reaction, the immobilized lipase can be recovered and used repeatedly as long as it does not lose activity.

In order to obtain an oil (triglycerides) containing a target triglyceride in which medium-chain fatty acids are bound to the 1,3-positions and a polyunsaturated fatty acid is bound to the 2-position, the immobilized enzyme is first separated from the reaction product, after which fatty acids bound to the 1,3-positions of the raw material oil or fat (triglycerides) severed during transesterification, and then medium-chain fatty acids in the form of an excess of reaction substrate, are removed from the reaction oil or fat. Examples of methods for removing said fatty acids and medium-chain fatty acids that can be used include the established methods of alkaline deoxidation, steam distillation, vacuum superfractionation, column chromatography, solvent extraction or any combination thereof. Furthermore, in the case of removing said fatty acids and medium-chain fatty acids from a large volume of oils and fats as in the case of production on a large industrial scale, they are preferably removed by superfractionation.

After removing free fatty acids in this manner, the resulting oil has a triglyceride content of 95% or more, and the triglyceride content can be further increased by removing the several percent of diglycerides and monoglycerides present in the oil by superfractionation and so forth. In addition, an ordinary oil purification treatment may also be performed, as necessary, and examples include deoxidation, degumming, decoloring and deodorizing.

Examples of oils and fats of the present invention include oils and fats containing 30-90 mol %, preferably 30-80 mol %, more preferably 45-80 mol % and most preferably 60-80 mol %, of triglyceride in which medium-chain fatty acids are bound to the 1,3-positions of the triglyceride, and at least one type of polyunsaturated fatty acid selected from the group consisting of a ω6 series polyunsaturated fatty acid having 18 or more carbon atoms and 3 or more double bonds and a ω9 series polyunsaturated fatty acid having 18 or more carbon atoms and 2 or more double bonds, is bound to the 2-position, and examples of polyunsaturated fatty acid bound to the 2-position include arachidonic acid, dihomo-γ-linolenic acid, 6,9-octadienoic acid, 8,11-eicosadienoic acid and 5,8,11-eicosatrienoic acid. Specific examples of oils and fats include oils and fats containing 25 mol % or more, preferably 30 mol % or more, and more preferably 40 mol % or more, of triglyceride in which medium-chain fatty acids are bound to the 1,3-positions of the triglyceride and arachidonic acid is bound to the 2-position, oils containing 5 mol % or more, preferably 10 mol % or more and more preferably 20 mol % or more, of triglyceride in which medium-chain fatty acids are bound to the 1,3-positions of the triglyceride and dihomo-γ-linolenic acid is bound to the 2-position, and oils and fats containing 5 mol % or more, preferably 10 mole or more, and more preferably 20 mol % or more, of triglyceride in which medium-chain fatty acids are bound to the 1,3-positions of the triglyceride and 5,8,11-eicosatrienoic acid is bound to the 2-position.

There are unlimited possibilities with respect to the applications of the aforementioned oils and fats of the present invention, such as oils and fats containing 25 mol % or more of triglyceride in which medium-chain fatty acids are bound to the 1,3-positions and arachidonic acid is bound to the 2-position, oils and fats containing triglyceride in which medium-chain fatty acids are bound to the 1,3-positions and dihomo-γ-linolenic acid is bound to the 2-position, or oils and fats containing triglyceride in which medium-chain fatty acids are bound to the 1,3-positions and ω9 series polyunsaturated fatty acid is bound to the 2-position, and it can be used as a raw material or additive of foods, beverages, cosmetics and pharmaceuticals. The oils and fats of the present invention are not subjected to any limitations whatsoever with respect to the purpose of its use and the amount used.

For example, examples of food compositions include not only ordinary foods, but also functional foods, nutritional supplement foods, pronatis formulas, infant formulas, baby food, foods to be consumed during pregnancy and geriatric foods. Examples of foods that contain oils and fats include natural foods that inherently contain oils and fats such as meats, fish and nuts, foods to which oils and fats are added during preparation such as soup, foods for which oils and fats are used as a heating medium such as doughnuts, oily foods such as butter, processed foods to which oils and fats are added during processing such as cookies, and foods in which oils and fats are sprayed or coated during final processing such as hard biscuits. Moreover, oils and fats can also be added to agricultural food products, fermented food products, livestock food products, marine food products or beverages that do not contain oils and fats. Moreover, these may also be in the form of functional foods or pharmaceuticals, examples of which include transintestinal nutrients, powders, granules, troches, medicines, suspensions, emulsions, syrups and other processed forms.

The following provides a more detailed explanation of the invention through its examples. However, the present invention is not limited to these examples.

EXAMPLE 1

(Imparting Heat Resistance by Immobilization of 1,3-Position Specific Type Lipase)

100 g of an ion exchange resin support (Dowex Marathon WBA, Dow Chemical) were suspended in 80 ml of a 12.5% aqueous solution of *Rhizopus delemar* (Talipase Powder, Tanabe Seiyaku Co. Ltd.) followed by drying under reduced pressure to obtain immobilized lipase. In addition, 25 g of a different immobilizing support in the form of a ceramic support (SM-10, NGK) were suspended in 100 ml of a 10% aqueous solution of *Rhizopus delemar* (Talipase Powder, Tanabe Seiyaku Co. Ltd.) followed by the gradual addition of 300 ml of cold acetone (−80°) while stirring to form a precipitate. This precipitate was then dried under reduced pressure to obtain immobilized lipase.

Next, 4 g of a microbial oil containing 40% by weight of arachidonic acid (containing 95% triglyceride, SUNTGA40S, Suntory Co. Ltd.), 8 g of caprylic acid, 600 mg of the aforementioned immobilized lipase and 240 µl of water were allowed to react for 48 hours while stirring (130 rpm) at 30° C. Following completion of the reaction, the reaction liquid was removed to obtain activated immobilized lipase.

This activated immobilized lipase was used in the following Examples 2, 3, 4, 5 and 7.

EXAMPLE 2

(Enzyme Stability Following Long-Term Reaction of Immobilized Enzyme)

0.48 g of immobilized enzyme (*Rhizopus delemar* lipase, support: Dowex Marathon WBA or SM-10) were added to a mixture (substrate) of 4 g of microbial oil containing 25% by weight of arachidonic acid (containing 95% or more triglyceride, SUNTGA25, Suntory Co. Ltd.) and 8 g of caprylic acid and allowed to react for 48 or 72 hours while stirring (130 rpm) at 30° C. followed by removal of the reaction oil or fat from the reaction product, addition of fresh substrate and repeating the same reaction for 80 days. After this long-term reaction, the same substrate as previously described was added to the recovered immobilized enzyme and allowed to react for 48 hours at 30° C. followed by extraction of triglyceride from the reaction oil or fat by alkaline hexane extraction at completion of the reaction. The caprylic acid (8:0) incorporated in the triglyceride and arachidonic acid (20:4) incorporated in the triglyceride were measured by GC analysis to determine the activity of the immobilized enzyme. The proportion of caprylic acid of the GC analyzed values (proportion in fatty acid composition: mol %) is shown in Table 1 as reactivity (enzyme activity), while the proportion of arachidonic acid of the GC analyzed values (proportion in fatty acid composition: mol %) is shown in Table 1 as residual specificity. As the immobilized lipase transesterifies fatty acids of the 1,3-positions of SUNTGA25 to caprylic acid, the amount of arachidonic acid remaining in the triglyceride is considered to represent the amount of arachidonic acid bound to the 2-position of the triglyceride.

TABLE 1

| Immobilized enzyme support | Reactivity Caprylic acid (mol %) | Residual specificity Arachidonic acid (mol %) |
|---|---|---|
| SM-10 | 36.9 | 19.9 |
| Dowex Marathon WBA | 44.5 | 18.5 |

Dowex Marathon WBA was indicated as being superior on the basis of these results. Namely, in comparison with SM-10, Dowex Marathon WBA did not exhibit a decrease in reactivity even after long-term reaction, and position specificity was comparable to that of SM-10. Thus, Dowex Marathon WBA can be easily surmised to be effective with respect to thermal stability as well.

EXAMPLE 3

(Production of 8A8 When Using as Raw Material Oil a Microbial Oil (Containing 95% or More Triglyceride, SUNTGA25, Suntory Co. Ltd.) Containing 25% by Weight Arachidonic Acid and Microbial Oil (Containing 95% or More Triglyceride, SUNTGA40S, Suntory Co. Ltd.) Containing 40% by Weight Arachidonic Acid [Enzyme Reaction Treatment Repeated 3 Times])

28 g of SUNTGA25 or SUNTGA40S, 56 g of caprylic acid and 4.8 g of immobilized lipase (*Rhizopus delemar* lipase, support: Dowex Marathon WBA) were allowed to react for 48 hours while stirring (130 rpm) at 30° C. Fatty acid bound to the 1,3-positions of the raw material oil (triglyceride) that were severed during transesterification and excess reaction substrate in the form of medium-chain fatty acid were present in the reaction oil from which the immobilized lipase had been removed, and by removing these fatty acids by alkaline hexane extraction, an oil subjected to one round of treatment was obtained. 12 g of the oil obtained from one round of treatment, 24 g of caprylic acid and 1.8 g of immobilized enzyme were allowed to react for 48 hours while stirring (130 rpm) at 30° C. An oil subjected to two rounds of treatment was obtained by removing the medium-chain fatty acids and so forth by the same treatment as previously described. Moreover, 3 g of the oil obtained from two rounds of treatment, 8 g of caprylic acid and 0.6 of immobilized enzyme were allowed to react for 48 hours while stirring (130 rpm) at 30° C. An oil subjected to three rounds of treatment was obtained by removing the medium-chain fatty acids and so forth by the same treatment as previously described.

The fatty acid compositions (mol %) of the reaction liquid in the case of using SUNTGA25 or SUNTGA40S for the raw material oil are shown in Tables 2 and 3.

TABLE 2

Raw Material Oil: SUNTGA25

| | 8:0 | 16:0 | 18:0 | 18:1 | 18:2 | 18:3 ω6 | 18:3 ω3 | 20:3 | 20:4 | 22:0 | 24:0 |
|---|---|---|---|---|---|---|---|---|---|---|---|
| Raw material oil | — | 14.89 | 6.15 | 13.90 | 23.81 | 2.10 | 2.29 | 2.95 | 23.47 | 1.70 | 3.40 |
| One treatment | 48.66 | 2.71 | 1.18 | 7.27 | 14.62 | 2.01 | 1.01 | 2.58 | 16.61 | 0.40 | 0.23 |
| Two treatments | 58.72 | 0.91 | 0.38 | 6.25 | 12.90 | 1.81 | 0.81 | 2.38 | 14.13 | 0.10 | 0.23 |
| Three treatments | 63.80 | 0.56 | 0.22 | 5.71 | 11.95 | 1.86 | 0.72 | 2.09 | 11.69 | — | 0.11 |

TABLE 3

Raw Material Oil: SUNTGA40S

| | 8:0 | 16:0 | 18:0 | 18:1 | 18:2 | 18:3 ω6 | 18:3 ω3 | 20:3 | 20:4 | 22:0 | 24:0 |
|---|---|---|---|---|---|---|---|---|---|---|---|
| Raw material oil | — | 13.65 | 6.01 | 15.07 | 7.30 | 3.59 | 0.21 | 4.50 | 37.70 | 2.03 | 3.74 |
| One treatment | 45.46 | 2.48 | 1.16 | 8.16 | 5.51 | 3.31 | — | 3.82 | 26.16 | 0.50 | 0.79 |
| Two treatments | 56.72 | 0.85 | 0.39 | 6.98 | 4.92 | 2.85 | — | 3.47 | 21.80 | 0.22 | 0.26 |
| Three treatments | 60.75 | 0.51 | 0.21 | 6.45 | 4.68 | 2.69 | — | 3.25 | 19.29 | 0.14 | 0.11 |

Since the composition of fatty acids bound to the triglyceride is represented as mol %, the mol % of caprylic acid if all of the fatty acids at the 1,3-positions of the raw material oil were transesterified to caprylic acid would be 66.6%. Thus, the proportion of caprylic acid was increased to 60% as a result of repeating the reaction.

EXAMPLE 4

(Analysis Method of 8A8)

Reactions have been reported in which the method for transesterifying fatty acids bound to the 1,3-positions of a raw material oil to medium-chain fatty acids using 1,3-position specific type lipase uses a fish oil or TGA-25 (SUNTGA25, Suntory Co. Ltd.) for the raw material oil. However, in both of these reactions, evaluations are made based on changes in the fatty acid composition (mol %) of an oil (triglycerides) obtained following the reaction indicated in Example 3 and, as triglyceride in which medium-chain fatty acids are bound to the 1,3-positions and polyunsaturated fatty acid is bound to the 2-position has not been analyzed, it was not possible to determine whether or not the invention had been carried out. In the present example, an analysis method is indicated using the example of 8A8, which is one of the target compounds of the present invention, in order to clarify the present invention.

8A8 is analyzed by quantifying by combining high-performance liquid chromatography (HPLC) and gas chromatography (GC).

[HPLC Analysis Method]

Column: Reversed phase column (Cosmosil 4.6×250 mm 5C18-MS)

Solvent: Acetone/acetonitrile (1:1), 1 ml/min

Analysis time: 55 minutes

Column oven temperature: 40° C.

Detector: Differential refractometer detector (cell temperature: 40° C.)

Sample: Injection of 5 μl of a 10% solution of oil (triglyceride) dissolved in chloroform

[GC Analysis Method]

Column: Frontier Ultra ALLOY UA-17-15M-0.1F (15 m×0.25 mm×0.1 μm)

Column temperature: 260° C.-(1C/min)-290° C.-(10° C./min)-390° C. (5 minutes)

Analysis time: 45 minutes

Injection port temperature: 310° C.

Detector temperature: 370° C. (hydrogen ionization detector)

Carrier gas: Helium

Linear velocity; 40 cm/min

Sample: Injection of 1 μl of a 1% solution of oil (triglyceride) dissolved in hexane When a triglyceride of the raw material oil in which arbitrary fatty acids are bound to the 1,2,3-positions is represented with XXX (X=arbitrary fatty acid), a triglyceride transesterified with one caprylic acid becomes XX8, and a triglyceride transesterified with two caprylic acids becomes 8X8. There are also triglycerides in which the fatty acid at the 2-position of 8X8 undergoes an intramolecular shift resulting in the formation 88X due to an intramolecular shift, and in that case, transesterification proceeds further resulting in the formation of 888.

In the case of the HPLC analysis, triglyceride can be separated at the molecular species level (however, AAP (triglyceride in which arachidonic acid is bound to the 1,2-positions and palmitic acid is bound to the 3-position) and APA (triglyceride in which arachidonic acid is bound to the 1,3-positions and palmitic acid is bound to the 2-position) cannot be distinguished and demonstrate the same retention times). This HPLC analysis makes it possible to calculate the proportions of 888, 8X8, XX8 and XXX. However, although the target 8A8 is present in the molecular species group of 8X8, since 8A8, 8D8 and 8G8 unfortunately exhibit the same retention times, they cannot be distinguished.

In the case of GC analysis, the 8A8, 8D8 and 8G8 that could not be distinguished with HPLC analysis can be distinguished (moreover, 8A8 and 88A can also be distinguished). However, although 888, 8X8 and XX8 can be detected, XXX cannot be detected as a result of decomposing.

Thus, the proportion of 8A8 in a triglyceride can be calculated by combining HPLC analysis and GC analysis.

The following results were obtained when the oil subjected to three rounds of treatment of Example 3 was analyzed.

|  | Proportion of 8X8 in oil (mol %) | Proportion of 8A8 in oil (mol %) |
| --- | --- | --- |
| Oil resulting from 3 rounds of enzyme treatment of SUNTGA25 | 92.5% | 18.9% |
| Oil resulting from 3 rounds of enzyme treatment of SUNTGA40S | 80.3% | 27.5% |

In this manner, the significance of the present invention was discovered for the first time through analysis of 8A8.

EXAMPLE 5

(Production of 8A8 Using SUNTGA40S for Raw Material Oil and Enzyme Reaction Temperature of 40° C.)

1 g of SUNTGA40S, 2 g of caprylic acid and 0.2 g of immobilized enzyme (*Rhizopus delemar* lipase, support: Dowex Marathon WBA) were allowed to react for 48 hours while stirring (130 rpm) at 40° C. Fatty acids bound to the 1,3-positions of the raw material oil (triglyceride) that were severed during transesterification and medium-chain fatty acids in the form of excess reaction substrate were present in the reaction oil following removal of the immobilized lipase, and these fatty acids were removed using the same method as Example 3 to obtain a treated oil. The fatty acid composition of resulting treated oil (mol %) is shown in Table 4. Furthermore, oil subjected to one round of treatment using the SUNTGA40S of Example 3 as the raw material oil is shown as a control for a reaction temperature of 30° C.

TABLE 4

| | 8:0 | 16:0 | 18:0 | 18:1 | 18:2 | 18:3 ω6 | 18:3 ω3 | 20:3 | 20:4 | 22:0 | 24:0 |
| --- | --- | --- | --- | --- | --- | --- | --- | --- | --- | --- | --- |
| Temperature: 30° | 45.46 | 2.48 | 1.16 | 8.16 | 5.51 | 3.31 | — | 3.82 | 26.16 | 0.50 | 0.79 |
| Temperature: 40° C. | 51.77 | 1.93 | 1.22 | 3.85 | 6.86 | 2.32 | — | 2.78 | 26.57 | 0.61 | 1.30 |

As a result of raising the reaction temperature from 30° C. to 40° C., substitution of caprylic acid increased from 45.46% to 51.77% and reactivity was enhanced.

EXAMPLE 6

(Production of Oil or Fat (Triglycerides) Containing 45% by Weight or More of Arachidonic Acid)

Using *Mortierella alpina* CBS754.68 for the arachidonic acid-producing microorganism, 1000 L of medium containing 2% glucose, 6% edible soybean protein, 0.3% $KH_2PO_4$, 0.05% $MgCl_2.6H_2O$, 0.05% $CaCl_2.2H_2O$ and 0.1% soybean oil (pH 6.0) were placed in a 2000 L aerated stir culturing tank, and aerated stir culturing was started under conditions of a temperature of 26° C., air flow rate of 1.0 vvm, stirring rate of 80 rpm and tank internal pressure of 1.0 kg/$cm^2$G. 5% glucose on days 1 and 2 of culturing, 4.5% glucose on day 3 and 1.5% glucose on day 4 were added sequentially. Moreover, the temperature was lowered to 21° C. on day 3 and culturing was continued at that temperature. The glucose was depleted on day 7, and culturing was continued until day 16. The proportion of arachidonic acid during the 16 days of culturing reached 61% by weight, and the amount produced (as arachidonic acid) was maintained at 12 g/L. Furthermore, as the proportion of arachidonic acid had already reached 60% by weight on day 13 of culturing, was sufficiently possible to shorten the duration of culturing. The resulting microorganisms were recovered by filtration and the oil or fat was extracted to obtain an oil or fat (triglycerides) containing 55% by weight or more of arachidonic acid (to be referred to as SUNTGA55).

EXAMPLE 7

(Production of 8A8 Using SUNTGA55 as Raw Material Oil and Enzyme Reaction Temperature of 40-41° C. [Continuous Reaction])

10 g of immobilized enzyme (*Rhizopus delemar* lipase, support: Dowex Marathon WBA) were filled into a jacketed glass column (1.8×12.5 cm, volume: 31.8 ml) and a continuous reaction was carried out by allowing a mixed oil consisting of SUNTGA55 and caprylic acid mixed at a ratio of 1:2 to flow through the column at a constant flow rate. Furthermore, the column temperature was set to 40 to 41° C. The flow rate and reaction efficiency of the aforementioned continuous reaction are shown as the mol % values of caprylic acid and arachidonic acid present in the resulting oil (Table 5).

TABLE 5

|  | 8:0 (Caprylic acid) | 20:4 (Arachidonic acid) |
| --- | --- | --- |
| SUNTGA55 | 0 | 57.00 |
| Flow rate (ml/h) | 8:0 (Caprylic acid) | 20:4 (Arachidonic acid) |
| 2.2 | 53.82 | 30.03 |
| 3.9 | 52.06 | 31.51 |
| 5.6 | 46.87 | 36.69 |
| 8.4 | 42.48 | 40.17 |
| 12.6 | 36.69 | 44.10 |
| 17.6 | 31.24 | 47.04 |
| 26.4 | 25.27 | 49.38 |
| 38.7 | 20.03 | 51.21 |

According to the results shown in Table 5, the reaction was carried out continuously for 92 days using a flow rate from 3.5 to 5.5 ml/h. Those results are shown in Table 6.

TABLE 6

| Number of days reacted | 8:0 (Caprylic acid) | 20:4 (Arachidonic acid) |
| --- | --- | --- |
| 1 | 49.60 | 34.32 |
| 2 | 53.00 | 31.22 |
| 10 | 51.75 | 32.87 |
| 20 | 50.10 | 34.61 |
| 35 | 48.15 | 36.08 |
| 50 | 46.73 | 37.37 |
| 70 | 46.44 | 37.43 |
| 80 | 43.90 | 39.43 |
| 92 | 41.43 | 40.99 |

Even under temperature conditions of 40-41° C., there were no sudden decreases in enzyme activity, and continuous production was achieved for 9.2 days.

The oil obtained with this continuous reaction was collected, and on day 92, when the fatty acids severed by the reaction and the medium chain fatty acids in the form of the reaction substrate were removed by molecular superfractionation, and the proportions of 8A8 and 888 in the oil were examined according to the method of Example 4, they were found to have reached 40.1 mol % and 7.31 mol %, respectively.

Although a similar continuous reaction was carried out using immobilized enzyme that used a different immobilizing support from that prepared in Example 1 (*Rhizopus delemar* lipase, support: Ceramic support (SM-10)), due to the low level of heat resistance of the immobilized enzyme, the mol % of caprylic acid in the oil obtained on day 30 after the reaction was started was 32.4%. Furthermore, when the proportion of 888 in the oil was examined according to the method of Example 4, it was found to have reached 11.6 mol %.

Thus, even if an oil having a high proportion of polyunsaturated fatty acid is used as the reaction raw material, as long as an immobilized enzyme of the present invention having heat resistance is used, production is possible at the practical level without suffering a decrease in reaction efficiency. In addition, as the proportion of 888 is clearly low, the position specificity of the enzyme was also clearly demonstrated to be adequately maintained despite raising the reaction temperature.

EXAMPLE 8

(Production of Triglycerides in which Medium-Chain Fatty Acids are Bound to the 1,3-Positions and Dihomo-γ-Linolenic Acid or ω9 Series Polyunsaturated Fatty Acid is Bound to the 2-Position When Using an Oil or Fat (Triglycerides) Containing Dihomo-γ-Linolenic Acid or ω9 Series Polyunsaturated Fatty Acid as Raw Material Oil or Fat at 40 to 41° C. of enzyme reaction temperature [Batch Reaction])

The inventors of the present invention established a production method of oils or fats (triglycerides) containing dihomo-γ-linolenic acid or ω9 series polyunsaturated fatty acid. An oil or fat (triglycerides) containing dihomo-γ-linolenic acid was obtained by using a microorganism having the ability to produce arachidonic acid and decreased Δ5 unsaturation activity [for example, mutant strain *Mortierella alpina* SAM1860 (NIBH Deposit No. FERM P-3589)] in accordance with the method described in Japanese Unexamined Patent Publication No. 5-91887, an oil or fat (triglycerides) containing ω9 series polyunsaturated fatty acid was obtained by culturing a microorganism having the ability to produce ω9 series polyunsaturated fatty acid [for example, mutant strain *Mortierella alpina* SAM1861 (NIBH Deposit No. FERM P-3590)] in accordance with the method described in Japanese Unexamined Patent Publication No. 5-91888, and an oil or fat (triglycerides) containing Mead acid was obtained by performing mutation treatment on a microorganism having the ability to produce arachidonic acid in accordance with the method described in Japanese Unexamined Patent Publication No. 10-57085. By culturing a mutant strain in which Δ12 unsaturation activity is decreased or missing, and at least Δ6 unsaturation activity and/or chain lengthening activity is enhanced [for example, *Mortierella alpina* SAM2086 (NIBH Deposit No. FERM P-15766)], an oil or fat (triglycerides) containing 8,11-eicosadienoic acid can be obtained by culturing a microorganism having the ability to produce ω9 series polyunsaturated fatty acid in a medium to which Δ5 unsaturation enzyme inhibitor has been added, or additionally culturing after adding Δ5 unsaturation enzyme inhibitor to a culture liquid in which said microorganism has been cultured, in accordance with the method described in Japanese Unexamined Patent Publication No. 5-91886.

1 g of an oil or fat (triglycerides) containing 44% by weight of dihomo-γ-linolenic acid (to be referred to as "SUNTGD"), 1 g of an oil or fat containing 16% by weight of 8,11-eicosadienoic acid (to be referred to as "SUNTG20:2") or 1 g of an oil or fat containing 24% by weight of 5,8,11-eicosatrienoic acid (to be referred to as "SUNTGM"), 2 g of caprylic acid and 0.2 g of immobilized enzyme (*Rhizopus delemar* lipase, support: Dowex Marathon WBA) were mixed and allowed to react for 48 hours while stirring (130 rpm) at 40° C. Fatty acids bound to the 1,3-positions of the raw material oil or fat (triglycerides) that were severed during transesterification and medium-chain fatty acids in the form of excess reaction substrate were present in the reaction oil or fat from which the immobilized enzyme had been removed, and these fatty acids were then removed according to the same method as Example 3 to obtain a treated oil or fat. The proportions of 1,3-capryloyl-2-dihomo-γ-linolenoyl-glycerol, 1,3-capryloyl-2-8,11-eicosadienoyl-glycerol or 1,3-capryloyl-2-5,8,11-eicosatrienoyl-glycerol in the resulting oil or fat Furthermore, in the present example, the immobilized enzyme was activated according to the same method as Example 1 using 4 g of raw material oil or fat, 8 g of caprylic acid, 600 mg of the aforementioned immobilized lipase and 240 µl of water.

EXAMPLE 9

(Application to Powdered Milk)

Powdered milk having enhanced absorption of arachidonic acid was prepared by mixing 0.3 g of triglycerides containing 40.1 mol % of the 8A8 obtained in Example 7 into 100 g of powdered milk.

EXAMPLE 10

(Application to a Fat Infusion Agent)

After adding 400 g of the triglycerides containing 40.1 mol % of the 8A8 obtained in Example 7, 48 g of purified egg yolk lecithin, 20 g of oleic acid, 100 g of glycerin and 40 ml of 0.1 N sodium hydroxide and dispersing with a homogenizer, distilled water for injection was added to bring to a volume of 4 liters. This was then emulsified with a high-pressure spraying emulsifier to prepare a lipid latex. After adding 200 ml aliquots of this lipid latex to plastic bags, the plastic bags were sterilized by high-pressure steam for 20 minutes at 121° C. to obtain fat infusion agents.

EXAMPLE 11

(Use of a Genipin Crosslinking Agent in Immobilization of 1,3-Position Specific Type Lipase)

After suspending 100 g of an ion exchange resin support (Dowex Marathon WBA: Dow Chemical) in 80 ml of a 12.5% aqueous solution of *Rhizopus delemar* lipase (Talipase powder: Tanabe Seiyaku Co. Ltd.) and gently stirring for 2 hours, 8 ml of a 5% aqueous solution of genipin were added after which gentle stirring was continued for 6 hours at room temperature. Subsequently, 240 ml of cold acetone (−80° C.) were gradually added while stirring to form a precipitate. This precipitate was then dried under reduced pressure to obtain immobilized enzyme.

A mixture 4 g of SUNTGA40S, 8 g of caprylic acid, 600 mg of the aforementioned immobilized lipase and 240 µl of water was allowed to react for 48 hours while stirring (130 rpm) at 30° C. Following completion of the reaction, the reaction liquid was removed to obtain activated immobilized enzyme.

EXAMPLE 12

(Enhancement of Heat Resistance by Using Genipin Crosslinking Agent in Activation of 1,3-Position Specific Type Lipase)

4.8 g of the immobilized enzyme obtained in Examples 1 and 11 (*Rhizopus delemar* lipase, support: Dowex Marathon WBA), 28 g of SUNTGA40S and 56 g of caprylic acid were allowed to react for 48 hours while stirring (130 rpm) at 30° C. The reaction oil or fat was removed from the reaction product followed by the addition of fresh substrate and reacting while stirring (130 rpm) for 480 hours at 30° C., 40° C., 50° C. and 60° C.

Subsequently, the reaction oil or fat was removed from the reaction product and fresh substrate was added in the same manner as previously described followed by allowing to react for 48 hours while stirring (130 rpm) at 30° C.

TABLE 7

Conversion Rate of 8:0 (Caprylic Acid) After Holding Immobilized *Rhizopus delemar* Enzyme Obtained in Example 1 for 480 Hours at Each Temperature

| Held temperature | Before holding for 480 hours | After holding for 480 hours | Activity retention rate (%) |
|---|---|---|---|
| 30 | 43% | 54% | 102 |
| 40 | 52% | 52% | 95 |
| 50 | 54% | 48% | 89 |
| 60 | 50% | 33% | 66 |

TABLE 8

Conversion Rate of 8:0 (Caprylic Acid) After Holding Immobilized *Rhizopus delemar* Enzyme Obtained in Example 11 for 480 Hours at Each Temperature

| Held temperature | Before holding for 480 hours | After holding for 480 hours | Activity retention rate (%) |
|---|---|---|---|
| 30 | 51% | 50% | 98 |
| 40 | 49% | 50% | 102 |
| 50 | 54% | 50% | 93 |
| 60 | 50% | 44% | 88 |

As a result, immobilized enzyme treated with genipin surprisingly retained 88% of its initial activity after holding for 480 hours at 60° C.

EXAMPLE 13

Based on the analytical results of Table 4, in the case of using SUNTGA25 (Suntory Co. Ltd.) containing 25% arachidonic acid for the raw material, the proportion of 8A8 in the oil following enzyme reaction was 18.9%. Moreover, when SUNTGA40S having a high content of arachidonic acid (triglycerides containing 40% arachidonic acid, Suntory Co. Ltd.) was used for the raw material, 27.5% 8A8 oil was obtained.

A study was conducted on enzyme immobilization in particular for the purpose of increasing the proportion of 8A8 in the oil following the enzyme reaction. As the support used for immobilization is a porous resin of an ion exchange resin (Dowex Marathon WBA), the load during enzyme immobilization can be changed over a certain range. Therefore, immobilized enzymes were prepared by making the amount of enzyme immobilized the same amount as Example 1, twice that amount and one-half that amount during immobilization of the enzyme in accordance with Example 1. Using each of these immobilized enzymes, 0.48 g of each immobilized enzyme was added to a mixed oil of 4 g of SUNTGA40S and 8 g of caprylic acid as raw materials in the same manner as Example 2, and allowed to react for 72 hours while stirring (130 rpm) at 30° C.

Table 9 shows the relationship between the amount of lipase contained in the immobilized enzyme and the proportion of 8A8 in the oil following completion of the reaction. Even when the enzyme reaction was repeated three times using SUNTGA40S, the same raw material as used in Example 4, the proportion of 8A8 in the oil was only 27.5%. On the other hand, in the case of the immobilized enzyme shown in Table 9 (using twice the amount of Example 1), the proportion of 8A8 in the oil or fat was able to be increased to 38.9% despite carrying out the reaction only once.

TABLE 9

| Enzyme content of immobilized enzyme* | Proportion of 8A8 in an oil (mol %) |
|---|---|
| ½ | 21.0 |
| 1 | 25.6 |
| 2 | 38.9 |

*Enzyme content is based on 10 g of Talipase powder per 100 g of the immobilized enzyme of Example 1, and is indicated as a multiple of that amount.

What is claimed is:

1. An oil or fat or triglyceride containing 30-90 mol % of triglycerides in which medium-chain fatty acids are bound to the 1,3-positions of the triglycerides, and at least one polyunsaturated fatty acid selected from the group consisting of 6,9-octadienoic acid, 8,11-eicosadienoic acid, and 5,8,11-eicosatrienoic acid is bound to the 2-position.

2. An oil or fat or triglyceride containing 5 mol % or more of triglycerides in which medium-chain fatty acids are bound to the 1,3-position of the triglycerides and dihomo-γ-linolenic acid is bound to the 2-position.

3. An oil or fat or triglyceride containing 5 mol % or more of triglycerides in which medium-chain fatty acids are bound to the 1,3-positions of the triglycerides and 5,8,11-eicosatrienoic acid is bound to the 2-position.

4. A food composition comprising blending an oil or fat or triglyceride according to claim 1 according to a special nutritional demand.

5. A food composition according to claim 4 wherein, the food composition is a functional food, nutritional supplement food, newborn formula, infant formula, baby food, food to be consumed during pregnancy or geriatric food.

6. An animal feed comprising blending an oil or fat or triglyceride according to claim 1.

7. A therapeutic nutritional food containing an oil or fat or triglyceride according to claim 1, and depending on the case, blended with a neutral carrier suitable for oral, intestinal or parenteral administration.

8. A pharmaceutical composition containing at least one oil or fat or triglyceride according to claim 1.

* * * * *